United States Patent
Seeger

(10) Patent No.: US 6,524,829 B1
(45) Date of Patent: Feb. 25, 2003

(54) METHOD FOR DNA- OR RNA-SEQUENCING

(75) Inventor: Stefan Seeger, Donau (DE)

(73) Assignee: Molecular Machines & Industries GmbH, Heidelberg (DE)

( * ) Notice: Subject to any disclaimer, the term of this patent is extended or adjusted under 35 U.S.C. 154(b) by 0 days.

(21) Appl. No.: 09/806,320

(22) PCT Filed: Sep. 29, 1999

(86) PCT No.: PCT/EP99/07209

§ 371 (c)(1),
(2), (4) Date: Jun. 18, 2001

(87) PCT Pub. No.: WO00/18956

PCT Pub. Date: Apr. 6, 2000

(30) Foreign Application Priority Data

Sep. 30, 1998 (DE) .......................................... 198 44 931

(51) Int. Cl.$^7$ ........................... C12P 19/34; C12Q 1/68; G01N 33/00; C07H 21/02; C07H 21/00
(52) U.S. Cl. .......................... 435/91.2; 435/6; 435/91.1; 436/94; 536/23.1; 536/25.3; 536/25.32
(58) Field of Search .......................... 435/6, 91.1, 91.2, 435/183; 436/94; 536/23.1, 24.3, 24.33, 25.3, 25.32

(56) References Cited

U.S. PATENT DOCUMENTS 6,136,543 A * 10/2000 Anazawa et al. .............. 435/6

FOREIGN PATENT DOCUMENTS

| EP | 0 381 693 B1 | 11/1995 |
| EP | 0 426 829 B1 | 9/1996 |
| WO | WO98/33939 | * 8/1998 |

OTHER PUBLICATIONS

Nakanishi et al., *DNA sequence for sequencing using fluorescence–labeled nucleotides.* Chem. Ab. 119:219181u (1993).

* cited by examiner

Primary Examiner—Ethan C. Whisenant
Assistant Examiner—Frank Lu
(74) Attorney, Agent, or Firm—Sughrue Mion, PLLC

(57) ABSTRACT

The invention relates to methods for the base sequencing of deoxyribonucleic acid or ribonucleic acid, comprising the following steps: (1) immobilising DNA or RNA single strands on a planar support; (2) focussing a laser beam on a single, immobilised single strand; (3) producing DNA or RNA complimentary strand of said immobilised, focused single strand by adding a solution containing (i) at least one luminescence-tagged nucleotide on the bases of adenine, cytosine, guanine and thymine for producing a DNA or RNA complementary strand or at least one luminescence-tagged nucleotide of the bases adenine, cytosine, guanine and uracil for producing an RNA complementary strand and (ii) a polymerase, each insertion of a luminescence-tagged nucleotide into the complementary strand being detected with a single-molecule detector and the luminescence signal of the previous luminescence-tagged nucleotide being deleted before the next luminescence-tagged nucleotide is inserted.

15 Claims, No Drawings

METHOD FOR DNA- OR RNA-SEQUENCING

The invention relates to a method for the base sequencing of deoxyribonucleic acid (DNA) or ribonucleic acid (RNA).

Today, the base sequencing of deoxyribonucleic acid (DNA) and ribonucleic acid (RNA) belongs to the most important analysis techniques in biotechnology, the pharmaceutical industry, food industry, medical diagnostics and other fields of application. The decipherment of the genomes of organisms offers the possibility of diagnosis, therapy and prevention of illnesses as well as the targeted modification of the human genome to generate organisms having modified characteristics. Sufficiently rapid sequencing methods are required to allow the use of this potential.

The classical sequencing methods according to Sanger et al (Proceedings of the National Academy of Science, USA, 74, 5463–7; 1997) as well as Maxam and Gilbert (Proceedings of the National Academy of Science, U.S.A., 74, 560–564; 1977), which are still today the basis for the standard sequencing methods, need 1 to 3 days for sequencing 200 nucleotides. This appears to be too slow, for example, for the problem to sequence the human genome with approximately $3 \cdot 10^9$ base pairs.

More recent attempts at accelerating sequencing methods have concentrated on methods in which individual nucleotides were detected using fluorescence spectroscopy. U.S. Pat. No. 4,962,037 discloses a sequencing method, according to which a complementary nucleic acid strand, where a fluorescence dye molecule characteristic for the base is bonded covalently to each base, is synthesized on a single strand. This nucleic acid fluorescence-tagged molecule is bonded to a particle surface, with the individual particles being held, for example, in a liquid flow with a microinjection pipette. Each fluorescence-tagged base is then successively cleaved from the nucleic acid strand by use of an exonuclease, and is guided in the liquid flow in the focus of a laser beam, where, after excitation, the fluorescence specific for the base is detected. The velocity of this sequencing method is limited theoretically only by the cutting rate of the exonuclease so that a sequencing velocity of 100 to 1,000 bases/seconds is assumed.

One precondition for the performance of the method disclosed in U.S. Pat. No. 4,962,037 is that only one single nucleic acid molecule is held to one single particle. The manipulation of a single particle with a single nucleic acid molecule is, however, technically very difficult and complicated and has proven not to be suited for practical applications. Furthermore, the use of an exonuclease is necessary which is able to cleave the dye-tagged nucleotides. This makes the development of this method more complicated and the use for this of modified exonucleases causes in addition as a rule an increased inexactness in the determination of the base sequence.

It is therefore the object of the invention to provide a method for base sequencing of DNA or RNA in which the advantages as regards the high velocity of a sequencing method with individual molecule detection, as is described in the prior art, is utilized but where at the same time the above-mentioned disadvantages are overcome.

To solve this object the invention provides a first method for base sequencing of DNA or RNA, comprising the steps:

(1) immobilizing DNA or RNA single strands on a surface;
(2) focussing a laser beam on a single, immobilized single strand;
(3) producing a DNA or RNA complementary strand of said immobilized, focussed single strand by adding a solution containing (i) a mixture of nucleotides of the bases adenine, cytosine, guanine and thymine for producing a DNA complementary strand or a mixture of nucleotides of the bases adenine, cytosine, guanine and uracil for producing a RNA complementary strand and (ii) a polymerase, with
  3a) at least two of the four nucleotides of the bases adenine, cytosine, guanine and thymine or at least two of the four nucleotides of the bases adenine, cytosine, guanine and uracil being differently luminescence-tagged in part or in full,
  3b) each insertion of a luminescence-tagged nucleotide into the complementary strand being detected with a single-molecule detector, and
  3c) the luminescence signal of the previous luminescence-tagged nucleotide being deleted prior to the insertion of the respective next luminescence-tagged nucleotide.

The invention further provides a second method for base sequencing of DNA or RNA, comprising the steps:

(1) immobilizing DNA or RNA single strands on a surface;
(2) focussing a laser beam on a single, immobilized single strand;
(3') producing a DNA or RNA complementary strand of said immobilized, focussed single strand by sequential addition of solutions containing respectively (i) one nucleotide of the bases adenine, cytosine, guanine and thymine for producing a DNA complementary strand or one nucleotide of the bases adenine, cytosine, guanine and uracil for producing an RNA complementary strand and (ii) a polymerase, with
  3a') the nucleotide contained in the solution being luminescence-tagged,
  3b) each insertion of a luminescence-tagged nucleotide into the complementary strand being detected with a single-molecule detector, and
  3c) upon detection of the insertion of a luminescence-tagged nucleotide in the complementary strand, the luminescence signal of the inserted nucleotide being deleted, and
  3d') rinsing occurring prior to the addition of the respective next solution.

The term DNA or RNA single strand designates according to the invention a non-hybridized DNA or RNA molecule. Such a single strand can be obtained by direct isolation from an organism including gene technology methods as well as by the treatment of such molecules with restriction enzymes. Oligonucleotides, PCR products and c-DNA count as these single strands. The production of the single strands from the double strands is known to the person skilled in the art, e.g. from J. Sambrook et al., "Molecular Cloning", $2^{nd}$ edition, Cold Spring Harbor Laboratory Press, 1989. The treatment with restriction enzymes can be performed directly before immobilization, which causes an immobilization of molecules with different base sequences. The single strands have preferably 5 to 2,000 bases, especially preferred is 100 to 1,000 bases. In principle, however, base lengths of up to 100 kilo-bases come under consideration.

In step (1) of the method according to the invention, the DNA or RNA single strands are immobilized on a surface. The surface is preferably the surface of a planar support which comprises the optical transparency necessary for the single molecule detection described below. A glass support is especially preferred, in particular a quartz glass support. In a preferred embodiment, the surface of the support, on which the single strands are immobilized, is chemically modified by application of a Langmuir-Blodgett film. A Langmuir-Blodgett film of a cellulose derivative is especially preferred, in particular trimethyl silylether cellulose cinnamate (TMSCC) and aminoalkyl trimethyl silylether cellulose (ATMSC).

The single strands can be be immobilized on the surface by adsorption, via a covalent bond as well as via a scavenger molecule. Scavenger molecules are in particular nucleotide oligomers which are immobilized on the surface and can bind the single strands by hybridization. The immobilization of the oligomer on the surface can take place by adsorption or by covalent binding to a chemically reactive group on the surface. The immobilization with the (strept-)avidin biotin technique is particularly preferred, with the oligomer being derived with biotine and binding to a (strept-)avidin molecule immobilized on the surface. The immobilization of the (strept-)avidin molecule is not restricted. In a preferred embodiment, the (strept-)avidin molecules are immobilized on the surface via a Langmuir-Blodgett film of a cellulose derivative. It is in particular preferred to coat the surface first with 1 to 8 mono-layers of aminoalkyl trimethylsilylether cellulose (ATMSC) and thereafter with 1 to 8 mono-layers trimethyl silylether cellulose cinnamate (TMSCC). The cinnamoyl groups of the TMSCC are then oxidized into aldehyde groups for the covalent coupling of the (strept-)avidin molecules. Furthermore, it is preferred according to the invention to use as scavenger molecules 5'-amino-modified oligonucleotides which bind directly to aldehyde groups, for example aldehyde groups obtained on Langmuir-Blodgett films in the above-mentioned manner.

Furthermore, it is preferred to immobilize on the surface the DNA or RNA single strands in step (1) such that the DNA or RNA single strands are present in a surface density of $\leq 1$ molecule/$\mu m^2$.

This surface density is set on the surface preferably by regulation of the surface density of covalent binding points. One possibility for this is offered by photo-crosslinkable Langmuir-Blodgett films, such as the TMSCC film described above, on which reactive groups, dependant on the irradiation time with UV light, develop on the surface. These reactive groups are then available for a covalent binding of DNA or RNA single strands, nucleotide oligomeres or (strept-)avidin molecules. The surface density of the single strands may as an alternative be set in the solution by the concentration of the single strands to be immobilized or by the oligomeres to be immobilized. The concentration depends here on the surface of the support as well as on the volume of the solution of the single strands to be immobilized or the oligomeres to be immobilized.

In step (2) of the method according to the invention, a laser beam is focussed on a single, immobilized single strand. The selection of the laser beam depends here on the luminescence tag of the nuclear bases used, which is described further below. To focus the laser beam on the immobilized single strand in step (2), one proceeds preferably in that (a) a luminescence-tagged nucleotide oligomere is hybridizised with the single strand, (b) the position of the hybridizised nucleotide oligomere is determined with a laser beam by scanning the surface on which the single strand is immobilized, and (c) the luminescence signal of the hybridizised nucleotide oligomere is thereafter deleted. Step (a) can be performed both prior to as well as after the immobilization of the single strand. The luminescence tag of the nucleotide oligomere and the laser beam are selected here such that in step (b) the luminescence tag is excited for luminescence. The scanning of the surface with the laser beam in step (b) can be performed with conventional grid or scanner devices, as are used for example in laser scanning microscopes. The deletion of the luminescence signal in step (c) can take place either by cleaving the luminescence tag, in particular photo-cleaving, or by photo-bleaching.

In step (3) of the first method according to the invention, a DNA or RNA complimentary strand of the immobilized, focussed single strand is produced by addition of a solution containing (i) a mixture of nucleotides of the bases adenine, cytosine, guanine and thymine for producing a DNA complementary strand or a mixture of nucleotides of the bases adenine, cytosine, guanine and uracil for producing an RNA complementary strand and (ii) a polymerase. The production of a polymer of the bases adenine, cytosine, guanine and thymine and/or the bases adenine, cytosine, guanine and uracil could also alternatively be carried out into synthetic nucleic acids, i.e. such nucleic acids which comprise no phosphate backbone but for example a peptide backbone (peptide nucleic acids). According to the invention, at least 2 of the 4 nucleotides of the bases adenine, cytosine, guanine and thymine or at least 2 of the 4 nucleotides of the bases adenine, cytosine, guanine and uracil are differently luminescence tagged in part or in full. It is particularly preferred that all 4 bases comprise different luminescence tags. This allows the determination of a base sequence with only a simple production of a complimentary strand. If only 2 of the 4 bases are differently luminescence tagged, the production must be repeated 5 times to obtain a complete sequence, with a different combination of tagged bases being used in each repetition. When using 3 different tagged bases the production of the complimentary strand must be repeated thrice with one different combination of tagged bases each.

In step (3') of the second method according to the invention a DNA or RNA complimentary strand of the immobilized, focussed single strand is produced by successive addition of solutions containing respectively (i) a nucleotide of the bases adenine, cytosine, guanine and thymine for producing a DNA complimentary strand or a nucleotide of the bases adenine, cytosine, guanine and uracil for producing a RNA complimentary strand and (ii) a polymerase, with the nucleotide contained in the solution being luminescence tagged. On the other hand, as an alternative, the production of a polymer of the bases adenine, cytosine, guanine and thymine or the bases adenine, cytosine, guanine and uracil into synthetic nucleic acids can also be performed, i.e. such nucleic acids which do not comprise a phosphate backbone but, for example, a peptide backbone (peptide nucleic acids). According to the second method according to the invention, the production of the complementary strand takes place by subsequent addition of the respective nucleotide solution, with it being rinsed before the addition of the respective next solution. If after the addition of the nucleotide solution a signal of a production should occur with the single molecule detector, the signal can thus be allocated to a certain base. If, for example, solutions containing a polymerase as well as, respectively, one nucleotide of the bases adenine, cytosine, guanine and thymine are added to the immobilized single strand, and if a signal is detected only with the addition of the second solution, i.e. the cytosine solution, the corresponding base of the immobilized single strand is thus guanine. If, on the other hand, a signal is detected during addition of both the second and the third solution, the sequence guanine cytosine is thus found on the immobilized single strand. Thus, the entire sequence of the immobilized single strand can be determined by repetition of the addition of the corresponding solutions.

The polymerase contained in the solution catalyses the production of the complimentary strand. Its selection is not restricted as long as it allows the production of the complimentary strand with the dye-tagged nucleotide. Examples of the polymerases which can be used according to the invention are native T4 polymerase, native T7 polymerase, the Klenow fragment of E.coli pol I, Exo III, E.coli pol III holoenzyme, the snake-venom phosphodiesterase and taq polymerase.

Each production of a luminescence-tagged nucleotide, catalysed by the polymerase, in the complimentary strand is detected according to the invention with a single molecule detector. The single molecule detector used according to the invention is not restricted as long as it allows with given detection volume, given wave length and output of the laser beam and given luminescence tag of the nucleotide the detection of a single luminescence-tagged nucleotide molecule. The requirements made as to sensitivity of the single molecule detector increase here with increasing detection volume and decreasing output of the laser beam. It is for this reason particularly preferred to minimize the detection volume in that the laser beam is focussed limited as to diffraction.

For the excitement of the luminescence tag laser light with a wave-length of 600 nm and more is preferred to minimize the occurrence of scattered light. In particular, semi-conductor lasers in this wave-length range are preferred for economic reasons for the method according to the invention. If the detection takes place via a fluorescence life time measurement, the laser used according to the invention is modulated, preferably pulsed.

The luminescence tag is set to the laser light used as well as the single molecule detector used. Fluorophores are preferably used according to the invention as luminescence tags. A suitable set of fluorophores (i.e. one fluorophore for each tagged nucleotide) is selected irrespective of the kind of detection. Differentiation is to be made here between the detection of the dye (i.e. the wave-length of the emitted photones) and the detection of the fluorescence life time of the fluorophore. Examples of dye sets for the detection of the fluorescence life time are described in S. Seeger et al., "Ber Bunsenges. Physikal. Chem." 97, 1542–1548, 1993, as well as in M. Sauer et al., "J. Fluorescence" 3, 131–139, 1993; examples for dye sets for the detection of the dye are described in L. M. Smith et al., "Nature" 312, 674–670, 1989, as well as J. M. Prober et al., "Science" 238, 336–341, 1987. For example, the dyes JA 22, JA 66, JA51-DS as well as the cyanine dye Cy5 (Amersham Pharmacia Biotech, Uppsala, Sweden) disclosed in Sauer et al., "J. Fluor. 5", 247–254, 1995, can be used for the detection of the fluorescence life time; the dyes FAM, JOE, TAMRA and ROX (Applied Biosystems, Foster City, Calif., USA) can be used for detection of the dyes. While in the first method according to the invention the luminescence-tagged nucleotides are tagged with different luminophores, the dye can be identical in the second method according to the invention for each nucleotide since the differentiation of the nucleotides is made possible by the difference of the respective solution. In view of a simplified excitement and detection, this manner of proceeding is preferred according to the invention.

The single-molecule detector comprises a projection lens, a unit which generates an electrical current upon the impact of a photon as well as a computer including software for evaluating electrical signals. The projection lens enables preferably a projection of emitted photons confocal to the focus of the laser beam onto the unit to generate an electrical signal. This unit is preferably a photodiode, particularly preferred is a single-photon counter avalanche photodiode. Alternatively, a photo-multiplier or an amplified CCD camera may be used. It is particularly preferred to set up the single molecule detector according to the invention in such a manner that detection only begins after a certain time after excitement by the laser ("gating"). A single molecule detector applicable according to the invention is described in L öscher et al., "Anal. Chem.", vol. 70, p. 3202–3205, 1998. For purposes of distinguishing dye, the single molecule detector is fitted with corresponding filters. For differentiation by way of measuring the fluorescence life time, preferably a detector is used that works in a time-correlated-single photon counting mode. Furthermore, rapid measurement electronics are required such as are found in, for example, SL Microtest GmbH, Jena.

In a preferred embodiment, the single molecule detector has an auto-correlation function. The auto-correlation function makes it possible to distinguish luminescence free of diffusing molecules from the luminescence on the immobilized nucleic acid strand and thus serves to increase the signal to noise ratio.

According to the invention, the detected luminescence signal of the inserted nucleotide is deleted prior to insertion of the respective subsequent luminescence-tagged nucleotide. This may occur by means of cleaving the luminescence tag, in particular by photo-cleavage. This is possible if the luminescence tag is bonded to the nucleotide via a light-sensitive group such as disclosed for example in WO 95/31429. In this case, a short laser pulse leads to cleavage of the luminescence tag. As a rule, a wavelength is used for cleavage which differs from that of the laser used to excite. Furthermore, it is preferred for the luminescence signal to be deleted by photo-bleaching the luminescence tag of the nucleotide. This may be achieved by, for example, a short-term increase in laser intensity, i.e. a short laser pulse.

Thus, the velocity with which the luminescence signal is deleted depends in particular on the output of the laser pulse as well as the duration of the time period between detection and laser pulse. Both parameters are easily controlled. To ensure that the luminescence signal of the inserted nucleotide is deleted before the insertion of the respective next nucleotide, these parameters are matched to the production velocity of the complimentary strand. The production velocity of the complimentary strand can be controlled by setting the temperature of the solution having a decisive influence on the polymerase activity and by setting the nucleotide concentrations.

If not all nucleotides are luminescence-tagged in the first method according to the invention, the base sequence of the immobilized single strand cannot be detected with a single production of the complimentary strand with sufficient exactness in the first method according to the invention. Consequently, the production must be repeated for determination of the complete sequence. This is performed preferably according to the invention on the same single strand. To carry this out the DNA or RNA complimentary strand produced as described above is cleaved from the immobilized DNA or RNA single strand by temperature increase and the method step (3) of the method described above is repeated. The method according to the invention thus allows the multiple performance of the sequence determination on the same molecule. This is advantageous even when using only luminescence-tagged nucleotides to increase the exactness of the sequence determination.

Alternatively, the method according to the invention can be repeated on a further single strand immobilized on the support. With single strands with the same base sequence this causes an increased exactness of the sequence determination. If the nucleic acids to be sequenced are treated before the immobilization with restriction enzymes, the successive determination of the various fragments of the single strand resulting due to this treatment is, however, also possible. Treatment with restriction enzymes can thus take place directly before the immobilization in the same reaction vessel.

EXAMPLES

First Example

With the step-wise binding of the single strand 1 ml of a $10^{-8}$ mol/l amino-functionalized oligonucleotide solution for approximately 4 cm² glass surface is incubated overnight in a PBS buffer; is then hybridized for 1 to 2 hours at a temperature gradient of 58° C. to 28° C. by the addition of 1 ml solution of the single strand in a hybridisation buffer; the dye-tagged oligonucleotide ($10^{-8}$ mol/l, 1 ml hybridisation buffer, temperature degree 28° C. to 4° C.) is then counter-hybridisized for 2–3 hours. This results in a density of approximately one molecule complex/10 $\mu m^2$.

Second Example

In the second manner of procedure, namely to perform the hybridisation step before the immobilization, the single strand, the amino-functionalized oligonucleotide and the dye-tagged oligonucleotide are mixed together in 1 ml buffer in a concentration of respectively $10^{-7}$ mol/l; finally, this solution is diluted to $10^{-10}$ mol/l and used for immobilization; this also results in a density of approximately 1 molecule complex/10 $\mu m^2$.

Third Example

2 $\mu l$ $10^{-11}$ M mononucleotides, tagged with the dye Cy5 (Amersham Pharmacia Biotech AB, Uppsala, Sweden), and 3.5 u P7-sequenase-polymerase were added to the immobilized single strand. The production of the nucleotide was detected with a laser output of 400 $\mu W$ and a focusing diameter of 2 $\mu m$.

What is claimed is:

1. A method for base sequencing of DNA or RNA comprising the following steps:
   (1) immobilizing DNA or RNA single strands on a planar surface;
   (2) focussing a laser beam on a single, immobilized single strand;
   (3) producing a DNA or RNA complementary strand of said immobilized, focussed single strand by adding a solution containing (i) a mixture of nucleotides of the bases adenine, cytosine, guanine and thymine for producing a DNA complementary strand or a mixture of nucleotides of the bases adenine, cytosine, guanine and uracil for producing a RNA complementary strand and (ii) a polymerase, wherein at least two of the four nucleotides of the bases adenine, cytosine, guanine, and thymine, or at least two of the four nucleotides of the bases adenine, cytosine, guanine, or uracil are partially or fully luminescence-tagged, said step (3) further comprising
   (a) detecting each insertion of a luminescence-tagged nucleotide into the complementary strand with a single-molecule detector, and
   (b) deleting the luminescence signal of the luminescence-tagged nucleotide after detection and prior to insertion of the respective next luminescence-tagged nucleotide,
   thereby base sequencing DNA or RNA.

2. A method for base sequencing of DNA or RNA comprising the following steps:
   (1) immobilizing DNA or RNA single strands on a planar surface;
   (2) focussing a laser beam on a single, immobilized single strand;
   (3) producing a DNA or RNA complementary strand of the immobilized, focussed single strand by sequential addition of solutions containing (i) one nucleotide of the bases adenine, cytosine, guanine and thymine for producing a DNA complementary strand or one nucleotide of the bases adenine, cytosine, guanine and uracil for producing a RNA complementary strand and (ii) a polymerase, wherein the nucleotide contained in the solution is luminescence-tagged, said step (3) further comprising
   (a) detecting each insertion of a luminescence-tagged nucleotide into the complementary strand with a single molecule-detector,
   (b) deleting the luminescence signal of the luminescence-tagged nucleotide after detection, and
   (c) rinsing the surface-immobilized DNA or RNA prior to the addition of each next solution,
   thereby base sequencing DNA or RNA.

3. A method according to claim 1, wherein for immobilizing of DNA or RNA single strands on a surface, the single strands are immobilized in step (1) by hybridization to nucleotide oligomers immobilized upon the surface.

4. A method according to claim 1, wherein during the immobilization of the DNA or RNA single strands, DNA or RNA single strands are immobilized on a surface in step (1) in a surface density of $\leq 1$ molecule/$\mu m^2$.

5. A method according to claim 4, wherein the surface density of the single strands is set on the surface by regulating the surface density of covalent bonding points for the attachment of the single strands.

6. A method according to claim 4, wherein the surface density of the single strands is regulated by the concentration of single strands to be immobilized or of the oligomers to be immobilized.

7. A method according to claim 1, wherein the step of focussing the laser beam on the immobilized single strand further comprises
   (a) hybridizing a luminescence-tagged nucleotide oligomer to the single strand,
   (b) determining the position of the hybridized nucleotide-oligomer by scanning the surface with a laser beam, and
   (c) deleting the luminescence signal of the hybridized nucleotide-oligomer after determining the position of the hybridized nucleotide-oligomer.

8. A method according to claim 1, wherein each insertion of a luminescence-tagged nucleotide into the complementary strand is detected in step (3a) by means of the fluorescence life time of the luminescence-tagged nucleotide.

9. A method according to claim 1, wherein each insertion of a luminescence-tagged nucleotide into a complementary strand is detected in step (3a) by means of the color of the luminescence-tagged nucleotide.

10. A method according to claim 1, wherein the single-molecule detector in step (3a) comprises an auto-correlation function.

11. A method according to claim 1, wherein deletion of the luminescence signal in step (3b) occurs by cleavage of a luminescence-tagged nucleotide.

12. A method according to claim 1, wherein deletion of the luminescence signal in step (3b) occurs by photobleaching the luminescence-tagged nucleotide.

13. A method according to claim 1, wherein the deletion of the luminescence signal is deleted is controlled by the output of the laser pulse used for deleting the luminescence signal and the duration of the time period between detection and laser pulse, these parameters being matched to the production velocity of the complementary strand which is controlled by the polymerase activity and the nucleotide concentration.

14. A method for base sequencing of DNA or RNA, wherein the complementary DNA or RNA strand produced according to claim 1 is disassociated from the immobilized DNA or RNA single strand by increasing the temperature, and the method according to one of the previous claims is repeated on the immobilized single strand.

15. A method for base sequencing of DNA or RNA, wherein said method according to claim 1 is repeated on an additional or the same DNA or RNA single strand immobilized on the surface.

* * * * *